United States Patent
Thomson et al.

(10) Patent No.: US 11,544,852 B2
(45) Date of Patent: Jan. 3, 2023

(54) PERFORMANCE SCANNING SYSTEM AND METHOD FOR IMPROVING ATHLETIC PERFORMANCE

(71) Applicant: Ectoscan Systems, LLC, Cincinnati, OH (US)

(72) Inventors: Paul E. Thomson, Cincinnati, OH (US); Mark F. Smith, Amelia, OH (US)

( * ) Notice: Subject to any disclaimer, the term of this patent is extended or adjusted under 35 U.S.C. 154(b) by 196 days.

(21) Appl. No.: 16/769,388

(22) PCT Filed: Dec. 4, 2018

(86) PCT No.: PCT/US2018/063840
§ 371 (c)(1),
(2) Date: Jun. 3, 2020

(87) PCT Pub. No.: WO2019/113064
PCT Pub. Date: Jun. 13, 2019

(65) Prior Publication Data
US 2021/0183063 A1    Jun. 17, 2021

Related U.S. Application Data

(60) Provisional application No. 62/595,346, filed on Dec. 6, 2017.

(51) Int. Cl.
*G06T 7/00* (2017.01)
*A63B 24/00* (2006.01)
*A63B 71/06* (2006.01)

(52) U.S. Cl.
CPC ........ *G06T 7/0016* (2013.01); *A63B 24/0062* (2013.01); *A63B 71/0622* (2013.01);
(Continued)

(58) Field of Classification Search
CPC ......... G06T 7/0016; G06T 2207/10024; G06T 2207/20076; G06T 2207/30196;
(Continued)

(56) References Cited

U.S. PATENT DOCUMENTS 4,054,824 A    10/1977 Nishioka
4,275,741 A    6/1981 Edrich
(Continued)

FOREIGN PATENT DOCUMENTS

CN    105750694    7/2016
JP    H10111300    4/1998
(Continued)

OTHER PUBLICATIONS

Del Bimbo et al., "Retrieval by Content Similarity of 3D Models Using Spin Images" Annales Des Telecommunications, Dec. 2005, vol. 60, Issue 11-12, pp. 1360-1378.
(Continued)

*Primary Examiner* — Khai M Nguyen
(74) *Attorney, Agent, or Firm* — Mark F. Smith; Smith Brandenburg Ltd.

(57) ABSTRACT

A performance scanning system that operates to detect and measure surface parameters of a portion of an athlete and uses the surface parameters to determine the likelihood that the athlete's physical performance has been or will be impaired.

20 Claims, 7 Drawing Sheets

(52) U.S. Cl.
CPC .............. *A63B 2071/0694* (2013.01); *A63B 2220/05* (2013.01); *G06T 2207/10024* (2013.01); *G06T 2207/20076* (2013.01); *G06T 2207/30196* (2013.01)

(58) Field of Classification Search
CPC ............ A63B 24/0062; A63B 71/0622; A63B 2220/05; A63B 2071/0694
See application file for complete search history.

(56) References Cited

U.S. PATENT DOCUMENTS

| | | | |
|---|---|---|---|
| 4,445,516 A | 5/1984 | Wollnik et al. | |
| 4,530,367 A | 7/1985 | Desjardins et al. | |
| 4,755,952 A | 7/1988 | Johns | |
| 4,986,664 A | 1/1991 | Iovoi | |
| 5,311,109 A | 5/1994 | Ozawa | |
| 5,325,449 A | 6/1994 | Burt et al. | |
| 5,428,444 A | 6/1995 | Haddock et al. | |
| 5,937,083 A | 8/1999 | Ostuni | |
| 5,941,833 A | 8/1999 | Lipman | |
| 6,057,925 A | 5/2000 | Anthon | |
| 6,484,047 B1 | 11/2002 | Vilsmeier | |
| 7,226,426 B2 | 6/2007 | Thomson | |
| 7,734,077 B2 | 6/2010 | Hirsch et al. | |
| 7,957,583 B2 | 6/2011 | Boca et al. | |
| 7,968,845 B1 | 6/2011 | Wagner | |
| 8,035,637 B2 | 10/2011 | Kriveshko | |
| 9,078,598 B2 * | 7/2015 | French | A61B 5/1128 |
| 9,633,433 B1 * | 4/2017 | Thomson | G06K 9/6201 |
| 10,512,420 B2 * | 12/2019 | Hyde | A61B 5/11 |
| 2002/0087274 A1 | 7/2002 | Alexander et al. | |
| 2002/0093115 A1 | 7/2002 | Jang et al. | |
| 2003/0013951 A1 | 1/2003 | Stefanescu et al. | |
| 2003/0091226 A1 | 5/2003 | Cahill et al. | |
| 2004/0019269 A1 | 1/2004 | Schaefer et al. | |
| 2005/0041843 A1 | 2/2005 | Sawyer | |
| 2005/0245839 A1 | 11/2005 | Stivoric | |
| 2005/0238589 A1 | 12/2005 | Houle et al. | |
| 2006/0206027 A1 | 9/2006 | Malone | |
| 2008/0026944 A1 | 10/2008 | Ray | |
| 2008/0253612 A1 | 10/2008 | Regler et al. | |
| 2008/0260202 A1 | 10/2008 | Roth | |
| 2008/0262869 A1 | 10/2008 | Bronn | |
| 2008/0269644 A1 * | 10/2008 | Ray | A61B 5/224 600/587 |
| 2008/0285831 A1 | 11/2008 | Kirchberg et al. | |
| 2009/0279672 A1 | 11/2009 | Reiner | |
| 2011/0082667 A1 | 4/2011 | Ibarz et al. | |
| 2011/0150342 A1 | 6/2011 | Franken et al. | |
| 2011/0205354 A1 | 8/2011 | Enomoto et al. | |
| 2012/0330447 A1 * | 12/2012 | Gerlach | G05B 19/0426 382/128 |
| 2015/0010128 A1 | 1/2015 | Drouin et al. | |
| 2016/0235374 A1 | 8/2016 | Miller et al. | |
| 2020/0108291 A1 * | 4/2020 | Piazza | G16H 50/70 |

FOREIGN PATENT DOCUMENTS

| | | |
|---|---|---|
| WO | WO 02/095382 | 11/2002 |
| WO | WO 2012/051394 | 4/2012 |

OTHER PUBLICATIONS

Huber, Automatic 3D Modelling Using Range Images Obtained from Unknown Viewpoints; IEEE Proceedings, 3rd International Conf. on 3D Imaging and Modeling, 2001, pp. 153-160.

Jurgen Assfalg et al., Content-Based Retrieval of 3D Objects Using Spin Image Signatures, Apr. 2007, pp. 589-599, vol. 9, No. 3, IEEE Transactions on Multimedia.

H. Quynh Dinh et al., "Multi-Resolution Spin-Images" 2006, Proceedings of the 2006 IEEE Computer Society Conference on Computer Vision and Pattern Recognition.

Berthold K. Horn, "Closed-Form Solution of Absolute Orientation Using Unit Quaternions" vol. 4, p. 629- , Apr. 1987, Optical Society of America.

Andrew Edie Johnson, "Spin-Images; A Representation for 3D Surface Matching" Aug. 13, 1997, Carnegie Mellon University.

International Search Report and Written Opinion for related application No. PCT/US11/01908 dated Apr. 4, 2012.

Furrow, Danies, :Scanning Thermal Optical Measurement Platform for Ulcer Detection In High-Risk Diabetic Pateients, Rensselare Polytechnic Institute, Trop NY, Aug. 2008.

Ismael Fernandez-Cuevas, et al., Infrared Thermography for the Detection of Injury in Sport Medicine, Springer Int. Pub., Chapter 4, pp. 81-109, 2017.

* cited by examiner

PERFORMANCE SCANNING SYSTEM AND METHOD FOR IMPROVING ATHLETIC PERFORMANCE

TECHNICAL FIELD

The subject invention is directed to a performance scanning system and method for use in training and more particularly, a performance scanning system and method detecting and measuring various surface changes, such as the inflammatory parameters, and preferably, deep scanning and performance scanning, for use in improving athletic performance and/or reducing the likelihood of injury to an athlete.

BACKGROUND

All athletes and their trainers want to improve their athletic performance. To this end, athletes and their trainers employ a variety of training methods, techniques, nutritional strategies, and supplements. Additionally, athletes often employ physicians, therapists, and other medical personnel to help improve athletic performance and/or to avoid injury. These medical professionals use known medical diagnostic methods, such as the physical exam, X-ray, and MRI to assess the athlete's body to check for incipient injury and to optimize the athlete's health for maximum performance. For example, if, on examination, an athlete's muscles are cold, a trainer or a therapist may apply heat wraps or use massage to loosen the muscle fibers and to improve circulation.

When athletic performance does diminish it could falter due to either "global" or whole-body factors, such as stamina or concentration, or it could fail due to "local" factors, such as the biomechanics or physiology of the body parts relevant to the athletic activity. For example, with repetitive throwing, baseball pitchers begin to develop changes in the tissues of the throwing arm, especially in the tissues of the elbow and the shoulder, that can not only lead to eventual injury, but which can also impede or diminish performance. Many of these tissue changes involve markers of inflammation, such as swelling, redness, warmth, and changes in range of motion. Until now, there has not existed a method or a device that could detect and measure these important inflammatory parameters (swelling, redness, warmth, and range of motion), especially during brief breaks in athletic activities or athletic contests (such as between innings in the case of baseball). Further, no prior art correlates surface markers and/or deep tissue changes or markers of inflammation with athletic performance. Accordingly, a need exists for an apparatus and a method to correlate tissue changes, such as, but not limited to, inflammatory parameters, with devices and methods to assess athletic performance and/or likeliness of injury with continued athletic activity. Such comparisons, analysis, or correlations could be used to assess an athlete's current status and to make predictions about future performance. It should be apparent to one skilled in the art that the present invention could also be used in non-athletes, animals, other such living organisms, or in anyone whose activities involve physical motion.

SUMMARY OF THE INVENTION

The subject invention is a performance scanning system that operates to detect and measure parameters, such as surface parameters, for example swelling or other surface contour changes, area, redness or other color changes, gloss, temperature, range of motion, of a portion of an athlete and uses the measured scanned parameters to determine the likelihood that the athlete's physical performance level has been or will be impaired.

In a preferred embodiment of the invention the performance scanning system includes one or more performance devices that operate to measure athletic performance level.

In a preferred embodiment of the invention the performance scanning system operates to quantify athletic performance.

In a preferred embodiment of the invention the performance scanning system operates to correlate measured scanned parameters with physical performance.

In another preferred embodiment of the invention the performance scanning system operates to determine if an athlete is physically at a condition to maximize athletic performance level.

In another preferred embodiment of the invention the performance scanning system operates to determine if an athlete is physically at a condition that increases the possibility of injury.

Another preferred embodiment of the invention is a method comprising the steps of taking one or more scans of one or more portions of an athlete's anatomy to obtained scanned parameters, comparing the scanned parameters to other scans (reference data) and/or reference performance data relating to the athlete, and using the comparison to determine the likelihood that the athlete's physical performance level has been impaired or will soon be impaired.

In a preferred embodiment of the invention the method includes measuring the performance of the athlete.

In another preferred embodiment of the invention the method includes correlating the performance of an athlete and the one or more scanned parameters of one or more portions of the athlete's anatomy to form a performance characteristic analysis record.

In another preferred embodiment, the method includes using a performance characteristic analysis record operates in conjunction with scanned parameters to determine the likelihood of injury or reduction in physical performance level of the athlete.

In another preferred embodiment of the invention the method comprises the step of scanning one or more portions of an anatomy of an athlete to obtained scanned parameters, comparing the scanned parameters to reference data (such as a set of reference scans or data) for that athlete and determining if the athlete's athletic performance level is likely to deteriorate beyond a certain level within a certain about of time.

In another preferred embodiment of the invention athletic performance level is the athlete's ability to pitch or throw a ball.

In another preferred embodiment of the invention athletic performance level is the athlete's ability to pitch or throw a ball at a certain speed.

In another preferred embodiment of the invention athletic performance level is the athlete's ability to pitch or throw a ball with a certain amount of accuracy.

In another preferred embodiment of the invention athletic performance level is the athlete's ability to run at a certain speed.

In another preferred embodiment of the invention athletic performance level is the athlete's ability to perform (such as for a non-limiting example, run at a certain speed for a certain amount of time).

In another preferred embodiment of the invention athletic performance level is the athlete's ability to swing a racket, bat, or other such means at a certain speed.

In another preferred embodiment of the invention athletic performance level is the athlete's ability to swing a racket, bat, or other such means at a certain speed for a certain amount of time.

A preferred embodiment of the invention is a performance scanning system for use in analyzing an athlete's physical performance, the performance scanning system comprises a computer system having a processor and memory, a data storage device in communication with the computer system, wherein the data storage device includes reference data, one or more scanning devices in communication with the computer system and operates to scan and obtain scanned parameters of one or more features, wherein the scanned parameters includes measurements of one or more surface features of an athlete, and wherein the computer system operates to compare the collected scanned parameters with the reference data and creates a recommendation that indicates the likelihood that the athlete's physical performance level is impaired.

In another preferred embodiment of the invention the scanning system further comprises one or more performance devices that operate to obtain performance parameters of an athlete and stores the performance parameters in the data storage device and wherein the computer system operates to correlate the performance parameters with the scanned surface parameters and makes a correlation between said performance parameters and the scanned surface parameters.

In a preferred embodiment of the invention the scanning system further comprises a deep scanning system that operates to obtain deep scanning parameters that correlates with surface parameters and the performance parameters and make a recommendation that indicates the likelihood that the athlete's athletic performance level has been impaired or likely to be impaired within a predetermined amount of time.

In a preferred embodiment of the invention the surface parameters are weighted in accordance with their impact on athletic performance level or an athlete's likelihood of sustaining injury.

Another preferred embodiment of the invention is a performance scanning system for use in analyzing an athlete's physical performance level, the performance scanning system comprises a computer system having a processor and memory and system software, an analysis software module, a data storage device in communication with the computer system and having performance reference data, one or more scanning devices in communication with the computer system and operates to scan a surface of a portion of an athlete's body and measure surface features and store surface parameters as collected data in the data storage device; wherein the analysis software module operates to compare the collected surface parameters with the performance reference data and creates a recommendation that indicates the likelihood that the athlete's physical performance level is impaired or will be impaired within a predetermined amount of time (or athletic activity).

A preferred embodiment of the invention is a performance scanning system for use in analyzing and predicting the physical performance of an athlete, the performance scanning system comprising: a computer system having a processor and memory, a data storage device in communication with the computer system, wherein the data storage device includes reference data, one or more scanning devices in communication with the computer system and operates to scan and obtain collected data of one or more features, wherein the collected data include scanned parameters of one or more surface features of an athlete, wherein the computer system then operates to compare the scanned parameters with the reference data to make a physical determination of the athlete and predicting the physical performance of the athlete.

In a preferred embodiment of the invention, the performance scanning system, the physical determination indicates the likelihood that the athlete's physical performance level is impaired.

In a preferred embodiment of the invention, the physical determination indicates the likelihood that the athlete's physical performance level will deteriorate after a calculated amount of time.

In a preferred embodiment of the invention, the physical determination indicates if the athlete is physically at a condition to maximize an athlete's athletic performance level.

In a preferred embodiment of the invention, the physical determination indicates if the athlete is physically at a condition that increases the possibility of injury to the athlete.

In a preferred embodiment of the invention, the reference data includes baseline parameters of surface features of a portion of the athlete prior to the athlete engaging in an athletic activity.

In a preferred embodiment of the invention, the reference data includes baseline parameters of surface features of a portion of the athlete taken at different time periods while the athlete is engaging in a physical activity.

In a preferred embodiment of the invention, the performance scanning system comprises one or more performance devices that operate to obtain performance parameters of an athlete and stores the performance parameters in the data storage device and wherein the computer system operates to use the performance parameters and scanned surface parameters to make a correlation between the performance parameters and the scanned surface parameters.

In a preferred embodiment of the invention, the performance scanning system further comprising a deep scanning system that operates to obtain deep scanning parameters, wherein the computer system operates to correlate the deep scanning parameters with surface parameters and performance parameters and makes a physical determination that indicates the likelihood that the athlete's athletic performance level has been impaired or likely to be impaired within a predetermined amount of time.

In another preferred embodiment of the invention the surface parameters are weighted in accordance with their impact on athletic performance level or an athlete's likelihood of sustaining injury.

In another preferred embodiment of the invention the computer system operates to make a recommendation based on said physical determination.

Another preferred embodiment of the invention is a performance scanning system for use in analyzing and predicting the physical performance of an athlete, the performance scanning system comprising a computer system in communication with an analysis software module, a data storage device having reference data, a scanning component having one or more scanning devices in communication with the computer system and operates to obtain collected data, wherein the collected data includes scanned parameters of a surface feature, wherein the analysis software module operates to compare the collected data with the reference data and creates a physical determination.

Another preferred embodiment of the invention, a performance scanning system for use in analyzing and predicting the physical performance of an athlete, the performance scanning system comprising: a computer system in communication with an analysis software module, a data storage device having reference data, a scanning component having one or more scanning devices in communication with the computer system and operates to obtain collected data, wherein the collected data includes scanned parameters of a surface feature and having deep scanning system that operates to obtain deep scanning parameters, wherein the analysis software module operates to compare the collected data with the reference data and the deep scanning parameters and creates a physical determination, wherein the physical determination indicates one or more of the following: the likelihood that the athlete's physical performance level is impaired, the likelihood that the athlete's physical performance level will deteriorate after a calculated amount of time, if the athlete is physically at a condition to maximize an athlete's athletic performance level, and if the athlete is physically at a condition that increases the possibility of injury to the athlete.

Other advantages, objects, and embodiments of the invention will be apparent from the following description, the accompanying drawings and the appended claims.

BRIEF DESCRIPTION OF THE DRAWINGS

To provide a more complete understanding of the present invention and further features and advantages thereof, reference is now made to the following description taken in conjunction with the accompanying drawings, in which.

BEST MODE FOR CARRYING OUT THE INVENTION

The subject invention is a new and novel performance scanning system that in a preferred embodiment that operates to acquire data and store and compare the acquired data to reference data and make a recommendation based on the comparison. As used herein, the term "athlete," unless otherwise stated, refers to both humans as well as animals. As used herein the term "feature" refers to a particular feature of an athlete, such as an arm, leg, elbow, kneel, foot, back and other anatomical parts of a body. The term "location" as used herein refers to a particular location on an athlete's body or a location on a feature.

Figure 1:
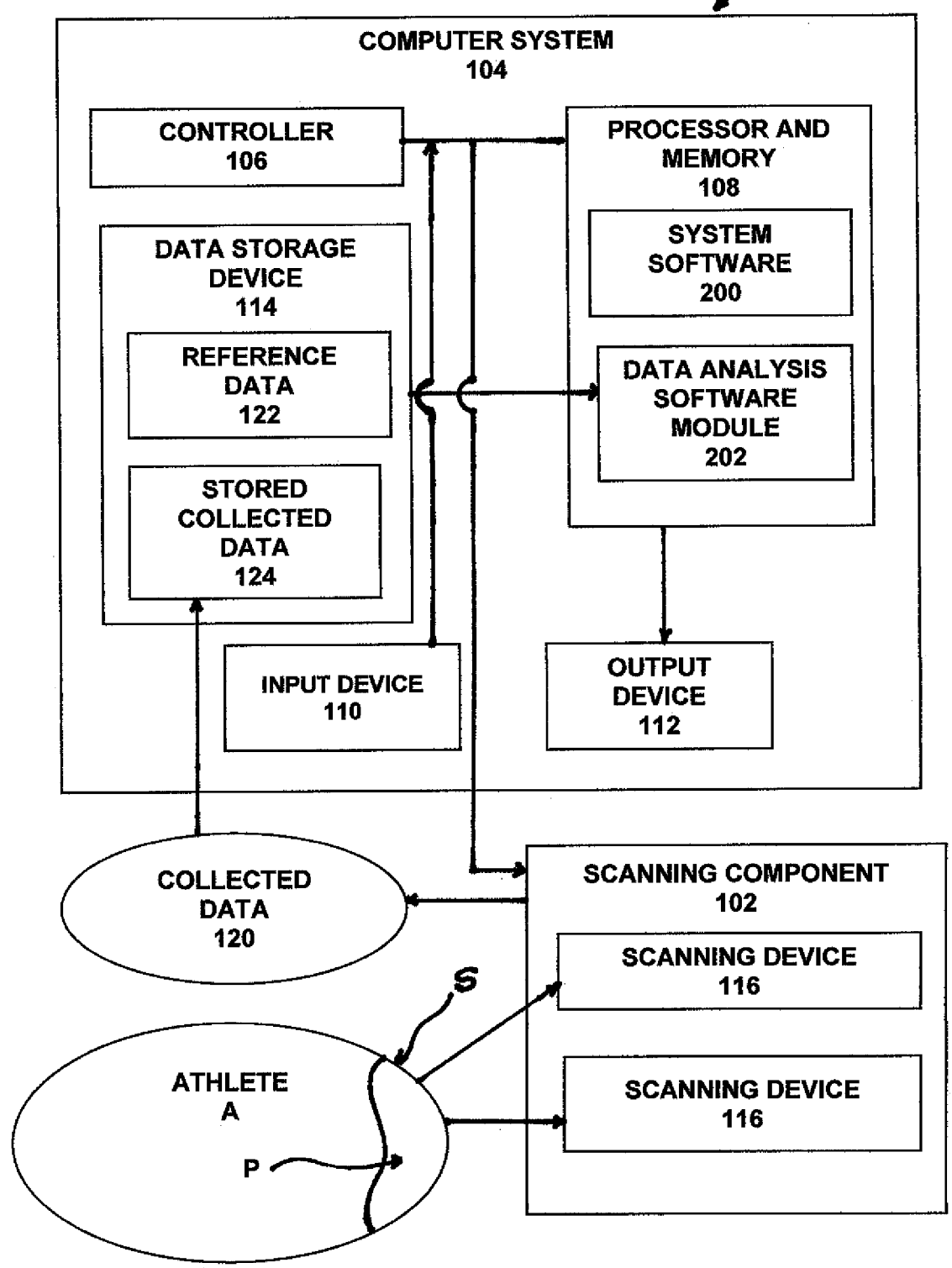
FIG. 1 is a schematic representation of a preferred embodiment of a performance scanning system for detecting and quantifying similarities or differences between collected data obtained from the scanned athlete and stored reference data showing a scanning component having one or more scanning devices and a computer system having at least one data storage device and at least one performance device that operates to indicate physical performance levels.

Referring to FIG. 1, in a preferred embodiment the performance scanning system 100 of the subject invention comprises a scanning component 102 and a computer system 104 for implementing and operating system software 200 that operates to perform a portion of the method of the subject invention. The computer system 104 includes a controller 106, a processor and a memory 108, and used for controlling the scanning operations of the scanning system and is electronically coupled to a data analysis software module 202 and a data storage device 114 that operates perform analysis of data and to store data (information). It should be understood that the processor and memory 108 of the computer system 104 operate in conjunction with the data analysis software module 202 and the data storage device 114 to perform the specific data analysis function as described herein. It should be understood that as used herein the term "computer system" includes any device capable for implementing and operating software and controlling the operation of various external devices, such as but not limited to various data acquiring devices, and performing the analysis (or cooperating with the data analysis software module) as described herein and can comprise various computing hardware such as central processing units (CPU's), graphics processing units (GPO's), digital signal processors (DSP's), microprocessors, field programmable gate arrays (FPGA's), very large scale integration (VLSI) systems, complex programmable logic devices (CPLD's), or systems on a chip (SOC's), and/or other such data processing devices including cell processors, biological processors, and quantum computing devices. The computer system 104 further comprises other devices, such as a suitable input device 110, like a keypad, touch screen, or any other suitable input device that can accept information; and one or more suitable output devices 112, such as a computer display, printer, image-forming or display device, and the like. The data storage device 114 can be in the form of any of the usual devices used for the storage of data, such as computer hard drives, floppy discs, binary codes, optical bits, mechanical scribes, magnetic tapes, compact discs, digital audio tapes, analog tapes, vinyl discs, and any device or devices capable of storing data. It should be understood that the computer system 104 can include any combination of the above components, or any number of different components, peripherals, and other devices. Preferably, the computer system 104 operates under the control of an operating system, such as the WINDOWS operating system developed by Microsoft Corporation or the MACINTOSH operating system developed by Apple Computer Corporation. It should be understood, however, that other operating systems could be utilized to implement the system software 200 of the performance scanning system 100 of the present invention.

Figure 3:
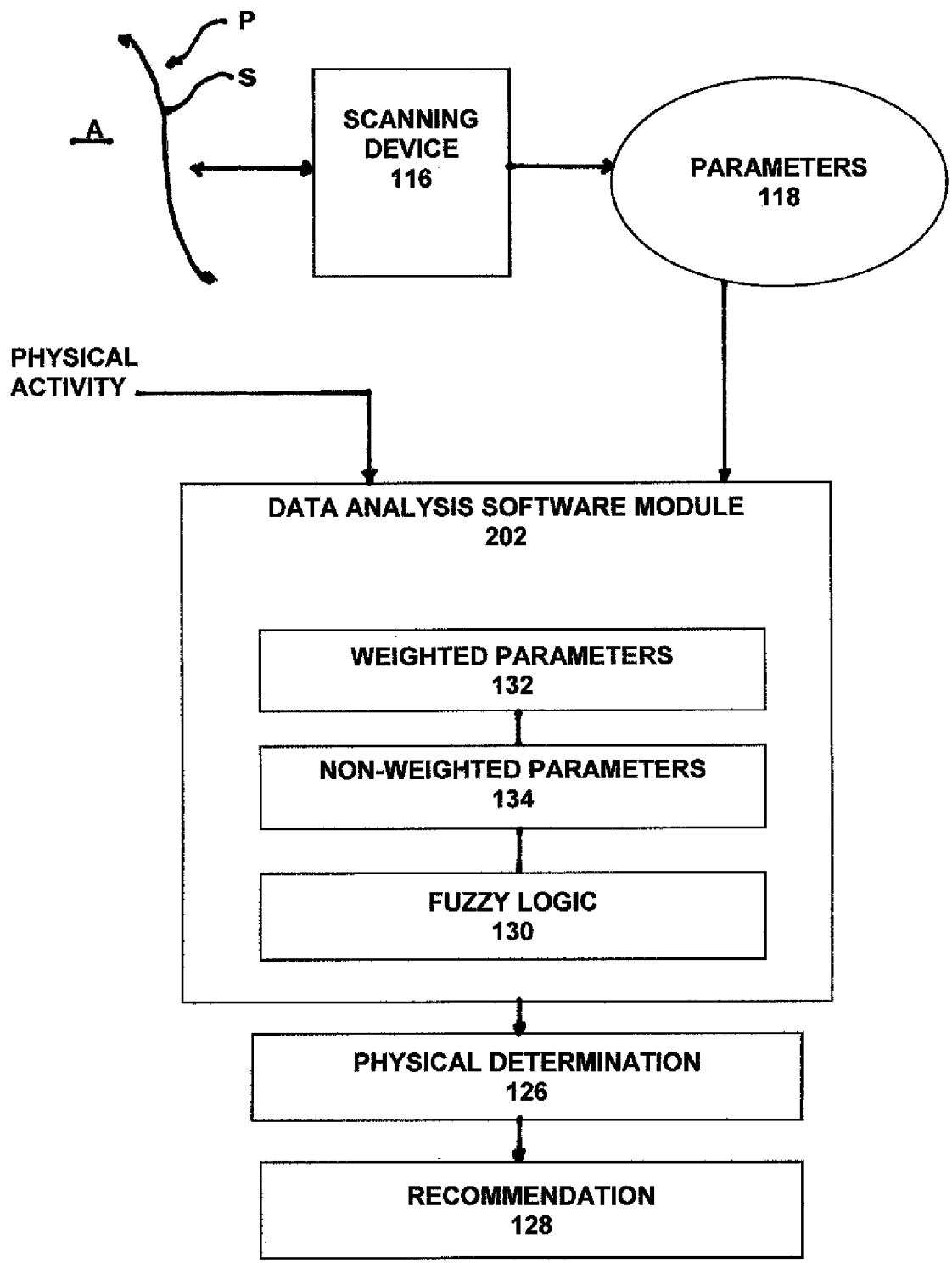
FIG. 3 is a schematic representation illustrating the general methodology showing the scanning device for obtaining scan parameters of the surface of an athlete for use by the data analysis software module as weighted parameters or non-weighted parameters and using fuzzy logic for making a physical determination and/or a recommendation.

Preferably, as shown, the scanning component 102 includes one or more scanning devices 116 that operate to scan surface features along the surface of a portion of an athlete and to directly or indirectly measure the various features of a portion P of an athlete A to obtain one or more scanned parameters 118 (FIG. 3). As used herein, scanned parameters 118 include, but are not limited to, measurements of color, temperature, texture, size, shape, spatial dimensions, contour, curvature, softness, roughness, shininess/gloss, infrared signature, electrical vectors/flux, magnetic field strength/vector/flux, dynamic rebound, flexibility, special phase characteristics, measurements derived from spatial phase characteristics, and other like parameters. In a preferred embodiment, the scanning devices 116 preferably comprise conventional scanning devices that have the capability to capture electromagnetic radiation from any part of the electromagnetic spectrum, and include, but not limited to visible light cameras, infrared cameras or detectors, ultraviolet cameras or detectors, x-ray or high-energy detectors, radio wave detectors, microwave detectors, structured light detectors, glossmeters, colorimeters, radiation dosimeters or reflectometers. The scanning devices 116 may also include microphones or other sound capturing devices, mechanical devices such as calipers or sensing wires or probes, laser distance or contour measuring devices, strain gauges or the like. It should be apparent to one skilled in the art that the scanning component 102 can comprise one or more scanning devices 116 capable of detecting and/or measuring features of an object (athlete) or any device capable of detecting or measuring features along (surface scanning) or through (deep scanning) the surface S of a portion P of an athlete A. The scanning component 102 may include one or more processors which are coupled to and communicates with and cooperates with the controller 106 of the computer system 104 or the scanning component 102 is directly controlled by the controller 106 and coupled to the controller 106 such as by electrical wires or other electrically conducting fibers or circuits, optical fibers, or any other wired or wireless data connection capable of transmitting data, sound waves, or images, including Internet connections, local area networks (LAN) connections, wide area networks (WAN) connections, which operate together to direct the operation of the scanning component 102 and the one or more scanning devices 116.

Figure 2:
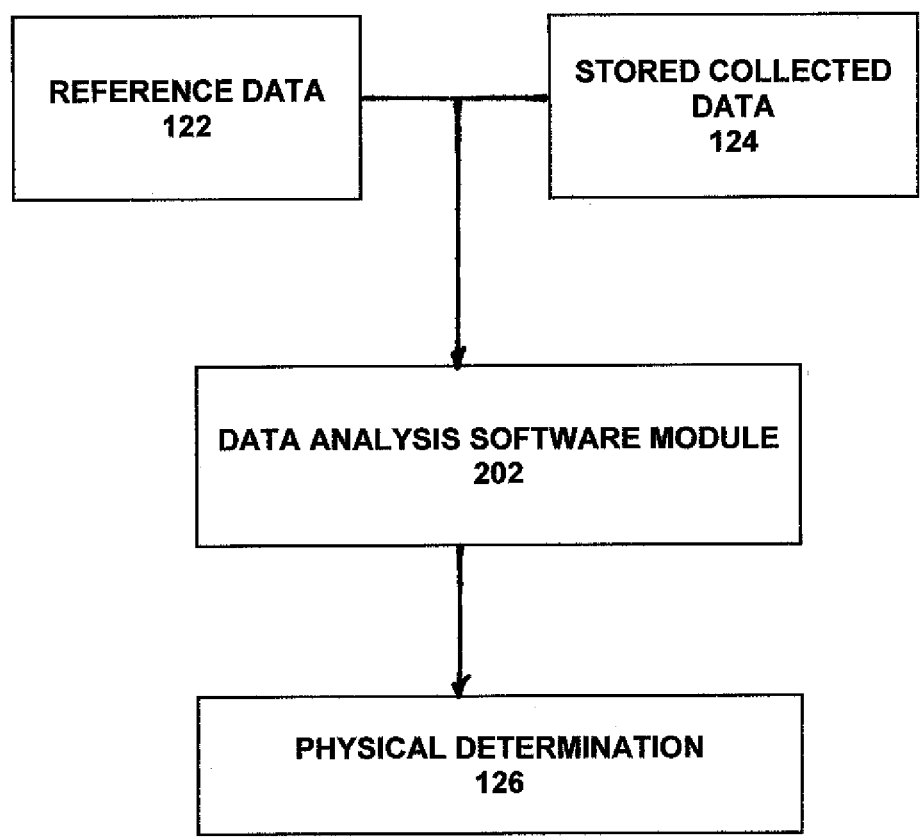
FIG. 2 is a schematic representation illustrating the general methodology of a preferred embodiment of the performance scanning system showing stored collected data and reference data for use by the data analysis software module for making a physical determination.

Referring to FIGS. 1 and 2, the computer system 104 is shown having a data analysis software (and/or firmware) module 202 which operates, as described below, to analyze stored collected data 124 of features retrieved from the scanned athlete A as well as using reference data 122 stored in the data storage device 114 within the computer system 104 (or within a memory (not shown) of the data analysis software module 202). It should be understood that as described and sued herein, reference data 122 includes data pertaining to a specific athlete and/or data pertaining to other similar athletes or athletes performing similar athletic activities. In a preferred embodiment, the data analysis software module 202 operates to identify (or uses inputted information) the scanned portion P of an athlete A and performs an analysis and makes a comparison using reference data pertinent for the same portion of the athlete. It should now be apparent to one skilled in the art that data analysis software module 202 can include various known information mechanisms (such as software) capable of performing the wide range of data analysis enabled by the usual range of available computer programs. It should also now be apparent to those skilled in the art that the performance scanning system 100 may comprise a variety of scanning devices and known databases and may be used for various purposes as will be described more fully herein.

Referring to FIGS. 1 and 2, the operating components of the performance scanning system 100 and the system software 200 is shown whereby the computer system 104 is in communication with the scanning component 102 such that instructions can be inputted into the system 100 using the suitable input device 110 to cause the system software 200 to direct the operation of one or more of the scanning devices 116. Preferably, the system software 200 is an interactive, menu and event driven system using conventional type of prompt, dialog, and entry windows to guide a user to enter information and instructions to provide an interactive communications interface between the system 100 and the users. As used herein, the term "software" refers to any form of programmed machine-readable language or instructions (e.g., object code) that, when loaded or otherwise installed, provides operating instructions to a machine capable of reading those instructions, such as a computer. The system software 200 of the present invention preferably can be stored or reside on, as well as be loaded or installed from, one or more floppy disks, CD ROM disks, hard disks or any other form of suitable non-volatile electronic storage media or can be run from a remote location such as a "cloud" or Internet site. The system software 200 can also be installed by downloading or other form of remote transmission, such as by using Local or Wide Area Network (LAN or WAN)-based, Internet-based, web-based or other remote downloading or transmission methods.

It should be understood that the scanning device 100 includes an output device 112 for use by a user in obtaining a desired output, such as analyzed data, images, recommendations, interventions and the like. Preferably the input device 110 and the output device 112 operate to input information and display data and conclusions (recommendations and physical determinations), respectively, and can comprise any of the usual SMS customary devices used for such operations, including but not limited to computer monitors and keyboards, cathode ray tubes, flat panel displays, handheld devices, digital cameras, film cameras, photosensitive panels, touchscreens, paper documents or other physical or virtual means of collecting/inputting/displaying data or conclusions, and so on. Paper records, anatomical drawings, photographs, pictures, or diagrams, 3D anatomical models, and/or various electronic recording ledgers can also be used to allow recording of the anatomical location of various symptoms and signs, either by the athlete or by his/her physician, coach, trainer, or therapist.

An illustrative example of a preferred embodiment of the performance scanning system 100 of the subject invention wherein one or more of the scanning devices 116 operate to take images of and/or measure various surface features (collected data) and include a visible light camera capable of detecting shape or form, and a color-detecting device, such as a colorimeter, a thermos camera capable of taking thermos images of a portion of a surface of an athlete. It should be understood that one or more of the scanning devices can be used to measure one or more of the surface features. The performance scanning system 100 as used herein operates such that a scanning device 116 operates to scan a surface S of a portion P of an athlete A to obtain collected data 120 and the scanning component 102 operates to transmit the collected data 120 to the data storage device 114 which stores the collected data 120 as stored collected data 124 for future processing by the data analysis software module 202. It should be understood that the collected data 120 includes various parameters of the scanned feature(s) and depends on the one or more scanning devices utilized for scanning the portion of the athlete. It should also be understood that the stored collected data 124 can also be stored and used as reference data 122. Preferably, reference data 122, which in a preferred embodiment includes a library of standard reference parameters, such as for example baseline parameters of features of the surface S of a portion P of the athlete A prior to the athlete engaging in an athletic activity or parameters of the surface S of a portion P of the athlete A taken at different time periods while the athlete is engaging in a physical activity. In a non-limiting example, as illustrated in FIGS. 1 and 2, after the collected data 120 is obtained and stored as stored collected data 124 in the data storage device 114, the data analysis module 202 operates to analyze the stored collected data 124 using the reference data 122 and makes a physical determination 126 such as the likely of the athlete having decreased performance (performance levels) or the likelihood that the athlete may be injured if the athlete continues with an athletic activity.

Data Analysis Software

Figure 4:
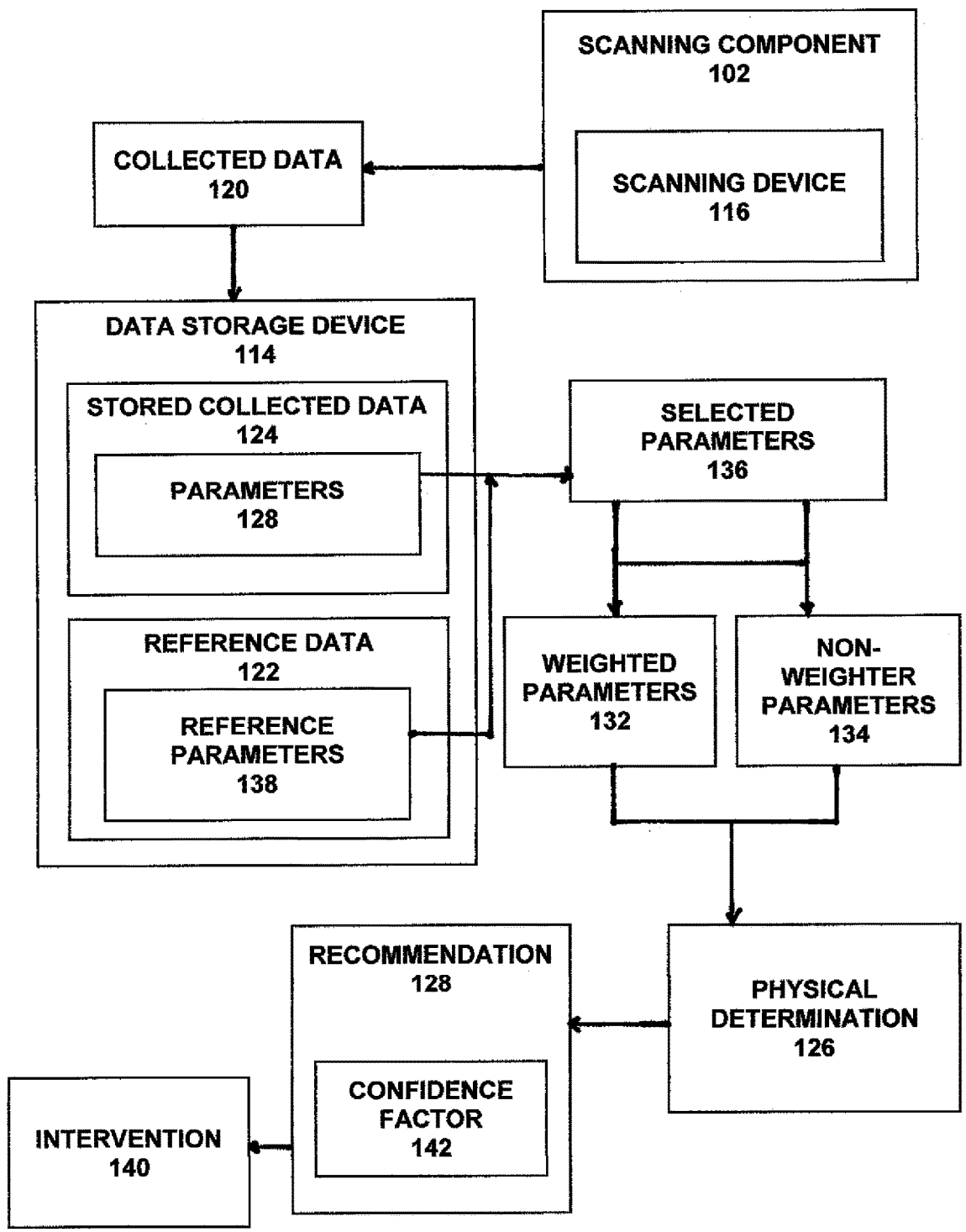
FIG. 4 is a schematic representation illustrating the general methodology of the scanning component having at least one scanning device performing a scan of the surface of an athlete and storing the collected parameters in the data storage device, selecting parameters, weighing the selected parameters and using reference data to make a physical determination and/or a recommendation and/or an intervention.

Referring to FIGS. 1 and 3, and as described above, the scanning component 102 includes one or more scanning devices 116 that operate to scan and/or directly or indirectly measure various features of a portion P of an athlete A to obtain scanner parameters 118. The data analysis software module 202 operates by utilizing fuzzy logic 130 and the various scanned parameters 118 (and preferably utilizing reference data 122) to determine and make a physical determination 126 and/or a recommendation (or provide the necessary instructions) 128 for various applications such as described herein. For an illustrative example the data analysis software module 202, operates using such scanned parameters 118, and depending on the feature of the portion P of the athlete A scanned and/or the physical activity being performed by the athlete, or the purpose of the analysis, one or more of the scanned parameters 118 can be weighted or non-weighted parameters, 132 and 134, respectively (FIG. 4). In a preferred embodiment of the invention the amount to weigh a scanned parameter 118 is given is based on the feature and/or the type and/or degree of a medical condition and/or the athletic activity. In a non-limiting illustration, inflammation occurring in a feature, such as the arm of a baseball pitcher or the legs of a race horse, it could be decided that the scanned parameters can include one or more of the cardinal signs of inflammation (color, temperature, swelling, loss of range of motion) and for the particular feature, a particular sign of inflammation can be weighted in determining the probability that the performance level of an athlete will deteriorate over a period of time or that there is a possibility that the athlete will be injured if the athletic activity continues. It should be understood that scanned parameters can be non-weighted (each parameter being equal in significance-non-weighted parameters 134) or can be weighted (a parameter having less or more significance that other parameters-weighted parameters 132). It should now be apparent to one skilled in the art that such determination as to weight can be placed into fuzzy sets based on known reference parameters and their know physical significance with respect to the athlete. The data analysis software module 202 then operates to compute and display a physical determination 126 based on the stored collected scanned data 124 in accordance with the non-weighted/ weighted parameters 134, 132, respectively, and sets of stored reference data 122. For this non-limiting example, scanned parameters 118 can be determined and weighted such that: for a swelling parameter, greater than a predefined amount is considered to be suspicious for decreasing performance or for the likelihood of injury developing; for a color parameter, any red, blue, or variegated color is considered to be suspicious; and for a temperature parameter, any temperature greater than reference temperature is considered to be suspicious. Accordingly, scanned parameters greater than a reference can be given a greater weight than a parameter below a reference. In addition, depending of the physical activity, a parameter, such as swelling, may be given a greater weight than a parameter such as color. In general, depending on a comparison of the stored collected data to reference data, the data analysis software module 202 further operates to determine and display a physical determination 126, such as on the output device 112 of the computer system 104. For a non-limiting example, as used herein a physical determination refers to the physical shape (for example, but not limited to, the amount of inflammation in a feature) and can indicate that the athlete is ready to perform a physical activity or that the athlete is not ready to perform a physical activity and requires additional "warm up." The physical determination can also be that the athlete remains injured or that the athlete is able to perform a physical activity. In a preferred embodiment, the data analysis software module 202 further operates, as described herein, to make a recommendation 128 based on the physical determination 126 and reference data 122 (such as a treatment or action that should be taken) such as in a non-limiting example to "stop any physical athletic activity or to continue any physical athletic activity." Accordingly, the subject invention operates to compare measurements (scanned parameters) of scanned features of a scanned portion of an athlete to a set of fixed reference data (reference parameters). The scanned parameters may be weighted or non-weighted and using the comparison makes a physical determination as to the physical condition of the athlete and calculates a recommendation based on the physical determination.

To further understand the operation of the data analysis software module 202 and the fuzzy logic 130 (FIG. 3) utilized, the following non-limiting exemplary illustration is provided. In a preferred embodiment of the invention, the performance scanning system 100 operates, such as shown in FIG. 4, whereby the scanning component 102 includes one or more scanning devices 116 effective for scanning a feature of an athlete to obtain collected data 120 and for transmitting the collected data 120 to the computer system 104 for storage in the data storage device 114 as stored collected data 124.

The data analysis software module 202 of the performance scanning system 100 uses stored collected data 124 and selects certain selected parameters 118 (selected parameters 136) from the stored collected data 124 that have a connection with determining the performance or physical condition of the athlete scanned. Using the selected parameters 136, the data analysis software module 202 further operates to determine if a selected parameter 136 should be weighted based on the feature scanned, the medical condition of the athlete and the athletic activity being performed, and if so, determines the weight to be given to the selected parameter 136 and compares the selected parameters 136 with reference parameters 138 stored as reference data 122 for the same feature to arrive at a physical determination 126 and preferably a recommendation 128. In a preferred embodiment of the invention, the system software 200 operates in cooperation with the data analysis software module 202 to generate a display on the output device 112 including the physical determination 126 and preferably a recommendation 128 as to the type of intervention 140 that should be applied as well as a confidence factor 142 as to the likelihood that the performance level of the athlete will deteriorate over a period of time or amount of continued athletic activity is included in that recommendation 128. In this non-limiting example, a possible recommendation 128 is to "Do Nothing" or "Continue the Athletic Activity." A possible intervention 140 can include "Resting for a period of time" or "apply ice to the affected area" or "apply heat to the affected area."

It should be readily apparent to one skilled in the art that the performance scanning system of present invention can be configured to operate in conjunction with various devices and apparatus, and for use in many applications. Further, it should be understood that in a preferred embodiment that the scanned parameters 118 are weighted based on the significance of the scanned parameter 118 in relation to portion P of the feature of the athlete A being assessed and condition being assessed and the importance that the scanned parameter 118 has in creating a physical determination 126 and a recommendation 128. It should be understood however that the various components and applications contained herein is for illustrative purposes and it should be understood that the systems and methods of the subject invention are not limited to the provided examples and listings. It should also be understood that the system is not limited to fuzzy logic systems but that other logic systems such as Bayesian logic, artificial neural networks, and other like systems can also be used.

Further, the data analysis software module operates to record, analyze, and display any or all important or relevant similarities, differences, correlations, or other information derived from comparing and analyzing either the subjective data of the athlete or other persons, the scan data, and the performance data or any combination thereof. Preferably, the data analysis software module can include or utilize commercially available statistical packages that can perform calculations/correlations/analysis/comparisons between two or more sets of data. It should be understood that these data could be digital, discrete, analog, or continuous. It should also be understood that the data analysis software module can also include or use unique/non-commercially available, proprietary formulae or flowcharts.

In another preferred embodiment of the invention the performance scanning system 100 of the subject invention further operates by performing two or more scans of a portion P (feature) of an athlete A and comparing the collected data 120 to determine changes in the portion P (feature) of the athlete A that has occurred during the period between the scans (period of time between obtaining collected data 120). It should be understood that as used herein the data collected in the first scan can be referred to as reference data and the data obtained in a second scan can be referred to as collected data. In another preferred embodiment, the subject invention operates by performing at least one scan of a portion P (feature) of an athlete A prior to the athlete performing a physical activity or after an athlete has performed a physical activity for a certain period of time and a scan at a later time and determines changes between the individual scans. One such system that can be used to compare scans, such as scanned images or scans obtaining different parameters, is shown and described in U.S. Pat. No. 9,599,461, issued on Mar. 21, 2017 and is incorporated herein in its entirety by reference.

Performance Scanning

Figure 5:
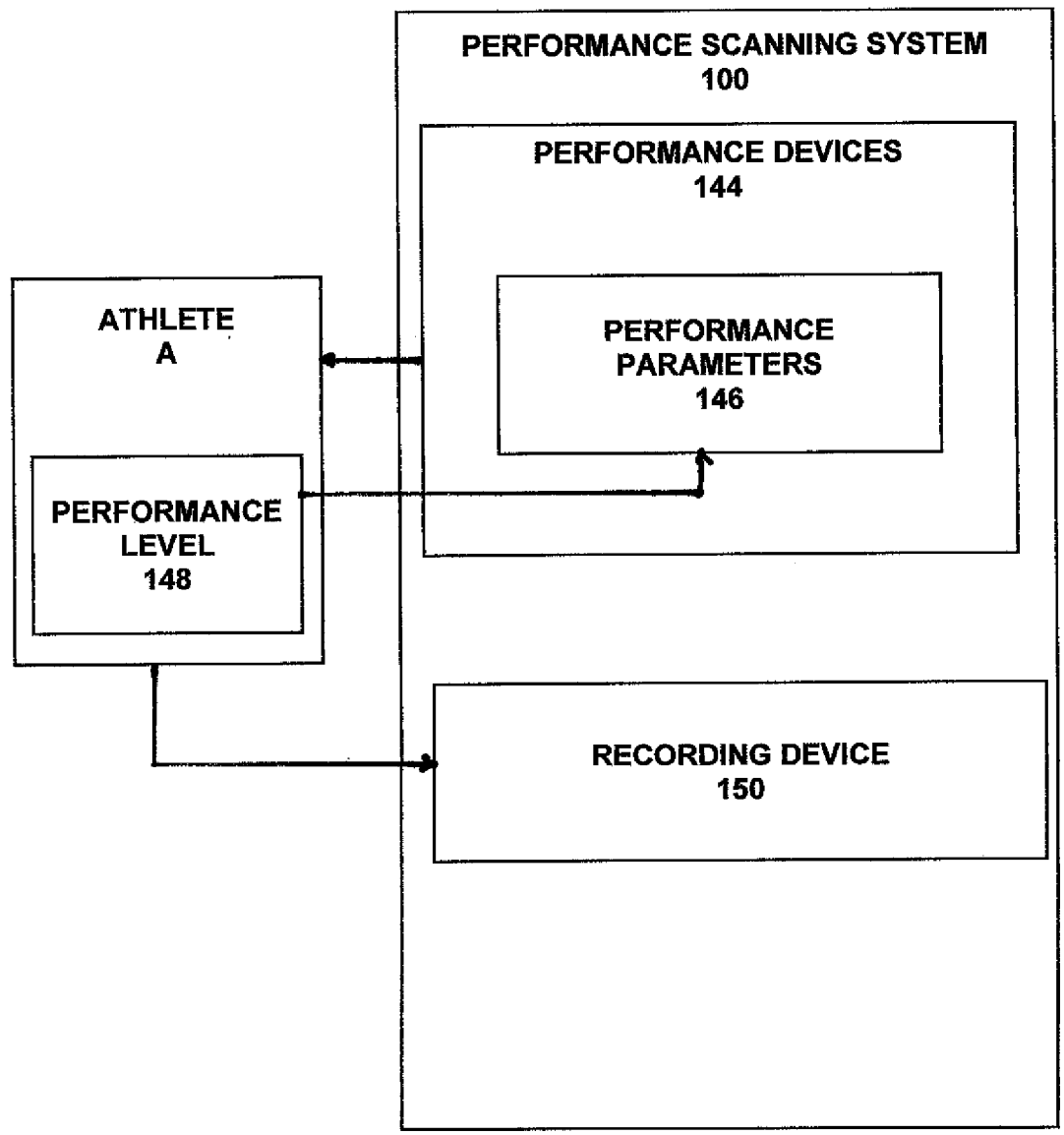
FIG. 5 is a schematic representation illustrating the general methodology of the performance scanning system showing performance devices for obtaining a performance level of an athlete and performance parameters.

In another preferred embodiment of the invention, as shown in FIGS. 4 and 5, the performance scanning system 100 operates to detect and to measure various changes in the scanned parameters 118 of an athlete A, such as in a non-limiting illustration one or more of the cardinal signs of inflammatory. As shown, the one or more scanning devices 116 operate to obtain collected data 120 which include the detection and measurements of certain scanned parameters 118, such as in a non-limiting illustration swelling or other surface contour changes, area, redness or other color changes, gloss, temperature, range of motion and the scanning component 102 transmits the collected data 120 (scanned parameters 118) to the data storage device 114 as stored collected data 124. Preferably, the performance scanning system 100 further includes one or more performance devices 144 that operate to measure and/or quantify performance parameters 146 of an athlete A. In a preferred embodiment, the performance scanning system 100 operates such that the scanned parameters 118 stored as stored collected data 124 and the performance parameters 146 are used together to calculate or determine a physical determination 126 of the likelihood that the athlete's physical performance and/or athletic performance level 148 has been impaired, or can or will continue to perform at a certain athletic performance level 148, or the likelihood that the athlete's athletic performance level 148 will deteriorate after a calculated or a certain amount of time or amount of activity. In another preferred embodiment of the invention the physical determination. 126 and recommendation 128 that indicate if the athlete is physically at a condition to maximize athletic performance level 148 and/or indicates if the athlete is physically at a condition that increases the possibility of injury to the athlete. For a non-limiting illustration, the data analysis software module 202 operates to corelate reference data (containing reference parameters) with performance parameters to determine when certain parameters correlate with an athlete's performance. For example, certain reference parameters may indicate that an athlete is experiencing inflammation and such inflammation reduces the athlete's performance level or increases the athlete's likelihood of injury. The data analysis software module operates that when certain parameters of the collected data (selected parameters) is compared with reference parameters (which has shown to indicate the athlete's performance is or will be reduced or the likelihood of injury increases), the data analysis software module operates to make a physical determination of the athlete, such as when the level of inflammation has reached a certain level, and makes a recommendation. In a preferred embodiment of the invention, the data analysis software module, using reference data, further displays on the output device an intervention based on reference data for that particular athlete and interventions which are known to be effective for that athlete for that particular physical determination.

As stated, in a preferred embodiment, the performance scanning system 100 includes one or more performance devices 144 that comprises conventional technologies available for measuring certain performance parameters 146 and include, but are not limited to radar, trajectory recording devices, videography, motion capture technology, high speed photography, optical recording devices, acoustical recording devices, human observation, and other such means. It should be understood that the various components of the system 100 communicate and are couple together by conventional communication apparatus such as by electrical, electronic, magnetic, acoustical or other devices, such as wires, conduits, fiber optics, Bluetooth, waveguides, and other such conventional means. The data analysis software module operates to correlate the performance parameters with reference data (reference parameters). For example, the various scans taken at different times of a feature or portion of an athlete, such as joints and/or tissue areas (deep surface data), can be aligned and differences between the scanned parameters (such as comparing scanned data to reference data) to make a physical determination if the athlete's condition, such as amount of inflammation is improving (becoming less inflamed) or deteriorating (becoming more inflamed) such that the data analysis software module operates to make a recommendation based on the athlete's physical performance level. For a non-limiting illustration, the physical determination can include the athlete's physical performance level, such as the athlete's ability to perform a physical activity, and a recommendation indicates based on if the athlete's physical performance level is impaired (such as beyond a threshold), and/or the amount of time that the athlete's physical performance level will deteriorate and reach a preset performance threshold, and/or that the athlete's physical condition and/or athletic performance level has maximized, and/or that the athlete is physically at a condition that increases the possibility of injury. In a non-limiting example, the athletic performance level can be athlete's ability to throw a ball or to throw a ball at a certain speed and/or accuracy, and/or to throw a ball for a certain amount of time with a certain amount of speed or accuracy, a recommendation can be made not to continue having the athlete continue performing the physical activity. In another non-limiting example, the athletic performance level can be the athlete's ability to run for a certain distance or at a certain speed or to swing a racket, bat or club at a certain speed or a certain amount of time, thus a recommendation can be made not to have the athlete continue performing an activity. For a non-limiting illustration, a physical determination can indicate an athlete's ability to pitch or throw a ball at a certain speed and/or accuracy, or to run at a certain speed and/or distance and/or for a certain amount of time, or to swing a device at a certain speed and/or for a certain amount of time and a recommendation can be made based on such a physical determination. It should be understood that the collected scan data (scanned parameters) can be correlated with the performance parameters such that when the scanned parameters match certain reference data (reference parameters), the athlete's performance level can be estimated as well as the likelihood that the athlete's performance level will deteriorate over a known period of time or that the likelihood that the athlete may sustain injury if the athletic activity continues. For a non-limiting illustration, if the scanned data (scanned parameters) indicate that inflammation has increased in a scanned feature and has reached a set threshold, the athlete's athletic performance level will drop within a certain amount of time or continued athletic activity.

In another preferred embodiment, the performance device is a recording device, which may be in the form of a paper or electronic diagram of the relevant body anatomical region (RAR) to record any physical problems, sensations, or symptoms present in the RAR. A physician or trainer may also make notations about any physical problems or signs they detect in the RAR. The scanning device 100 then operates to scan the RAR and stores the RAR as collected data 120 in the data storage device 114. After collecting data using one or more scanning devices, a recommendation can be made that the athlete performs or modified his/her athletic and/or warm-up activity and/or training and/or rehabilitation activity. During this activity, one or more additional performance devices are used to assess the athletic/training/warm up/rehabilitation activity. Trainers or therapists may also assess the activity via their own naked eye or palpation methods. Then, the athlete and/or physician or other personnel again records additional data, such as relevant symptoms, signs, sensations, or other problems which is stored as collected data in the data storage system. After storing the collected data, the performance scanning system further operates to obtain surface and/or deep collected data. After all of the above described collected data has been stored in the data storage device, the data analysis software module operates to correlate the collected data (scanned parameters) with reference data (reference parameters) and performance parameters and derive and display a physical determination of the athlete and creates a recommendation based on the physical determination. It should now be understood to one skilled in the art that in a preferred embodiment the system operates to link subjective data and objective data (collected data and reference data) to each other and to performance parameters. For a non-limiting illustration of the operation of the data analysis software module, the data analysis software module operates to use a correlation formula of the general form: k(RAR scan data) equals performance parameters, where "k" is a constant of proportionality. For instance, k(RAR temperature) equals speed. It should be understood that k may be constant for all athletes performing the same activity or it could be unique to each athlete or for each type of activity. It should now be understood to one skilled in the art that a variety of mathematical relationships may exist between the various collected data and athletic or physical performance. It should also be understood that such mathematical relationships may also be in the form of f(RAD scan data) where f is a linear or nonlinear function or operator.

Deep Scanning

Figure 6:
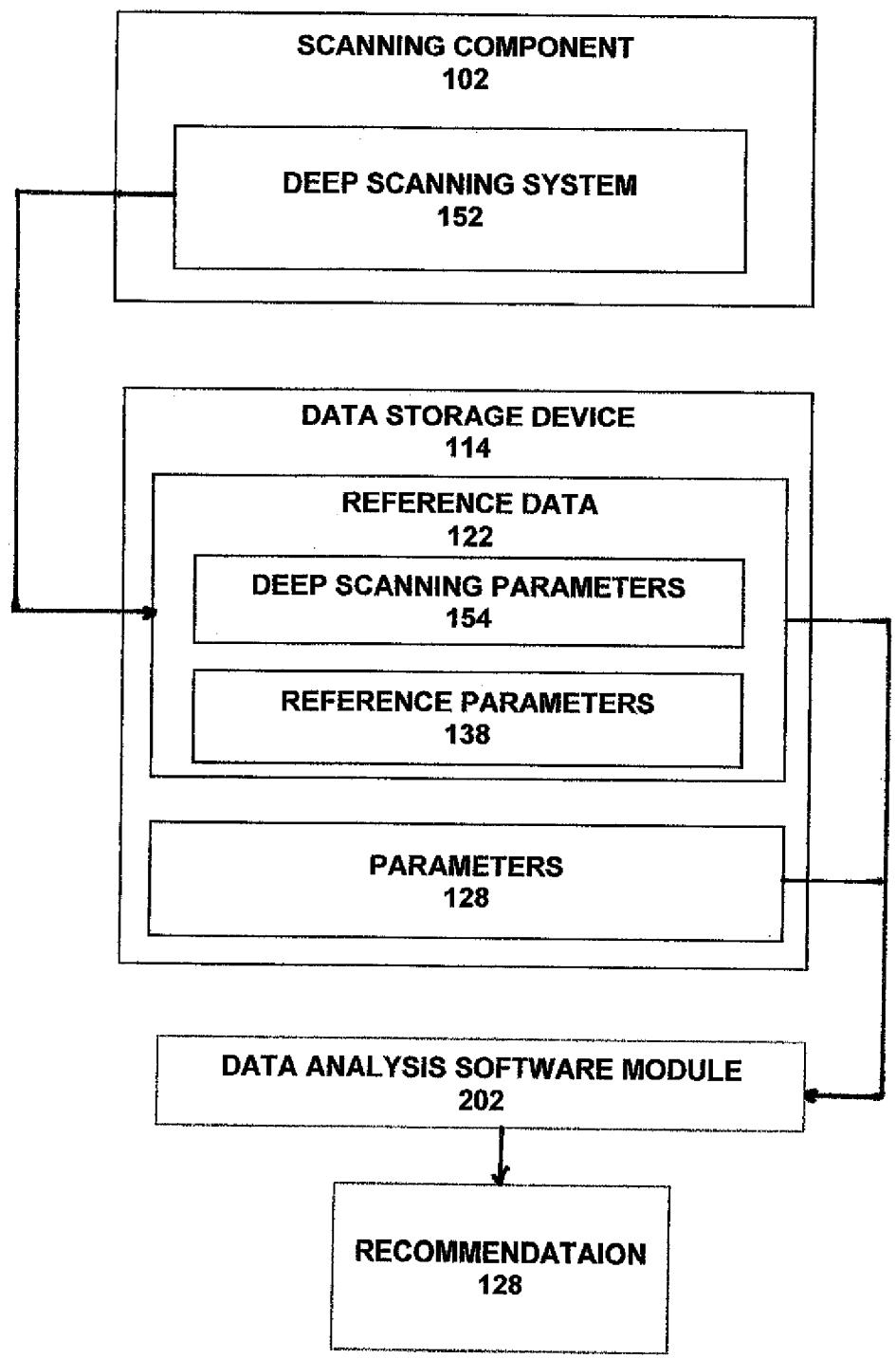
FIG. 6 is a schematic representation of the scanning component having a deep scanning system for obtaining deep scanning parameters of an athletic and using the deep scanning parameters, scanned parameters and reference parameters for use by the data analysis software module for making a recommendation.

In a preferred embodiment of the invention, as shown in FIG. 6, the scanning component 102 also includes a deep scanning system 152 that is utilized to perform deep scanning (scanning of deep layers of anatomy lying below the skin and the subcutaneous layers) to derive deep scanning parameters 154. This deep scanning system 152 may comprise any of the usual technologies available for such work, including but not limited to MRI, CT, ultrasound, X-ray, tomography, electrical field/vector devices, or acoustical scanners or microphones. In a preferred embodiment of the invention the performance scanning system 100 operates such that the data analysis software module 202 utilizes and correlates scanned parameters 118 (surface scanned data and deep scanning parameters) and performance parameters 146 (and other pertinent reference data 122) to makes a physical determination 126 of the likelihood that the athlete's athletic performance level 148 has been impaired, or can or will continue to perform at a certain athletic performance level 148, or makes a recommendation 128 based on the likelihood that the athlete's athletic performance level 148 will deteriorate after a certain amount of time or activity.

Non-Limiting Examples

As previously described, the data analysis software module of the performance scanning system operates as a performance scanner and uses scanned collected data of parameters that have or have not been weighted to compare with stored reference data. In a preferred embodiment of the invention the stored reference data includes performance parameters correlated with previously obtained reference parameters to define (calculate) an athletic performance level. In a non-limiting example, with repetitive throwing, baseball pitchers begin to develop changes in the tissues (features) of the throwing arm (location), especially in the tissues of the elbow and the shoulder, that can not only lead to eventual injury, but which can also impede or diminish performance. Many of these tissue changes involve markers of inflammation, such as swelling, redness, warmth, and changes in range of motion. The performance scanning system operates to scan and measure one or more of these important inflammatory surface scanned parameters (such as, but not limited to swelling, redness, warmth, and range of motion) using one or more scanning devices. Such surface scanned parameters are then compared to previous surface scanned parameters (reference parameters) that have been correlated with the athlete's athletic performance level and makes a physical determination. For a non-limiting example, as inflammation develops in the athlete's elbow and/or shoulder, the athlete's ability to pitch accurately or to throw a ball with speed diminishes (which can be pre-determined by comparing performance parameters with stored reference parameters), thus the athlete's performance level decreases. Accordingly, using surface scanned parameters and comparing to previous surface scanned parameters (reference parameters) and correlating with performance parameters obtained for the athlete, a user can anticipate when the athlete's performance level will drop below a threshold amount and make a recommendation. In another non-limiting example, by comparing surface scanned parameters with previous surface scanned parameters (reference parameters) and correlating with performance parameters obtained for the athlete, a recommendation can be created as to when the athlete should stop participating in order to avoid a drop in the athlete's performance or that the likelihood of injury increases above a threshold. Accordingly, it should now be apparent to one skilled in the art that such comparisons, analysis, and correlations can be used to assess an athlete's current status (physical determination) and to make predictions about future performance. It should also now be apparent to one skilled in the art that the present invention could also be used in non-athletes, animals, other such living organisms, or in anyone whose activities involve physical motion.

Figure 7:
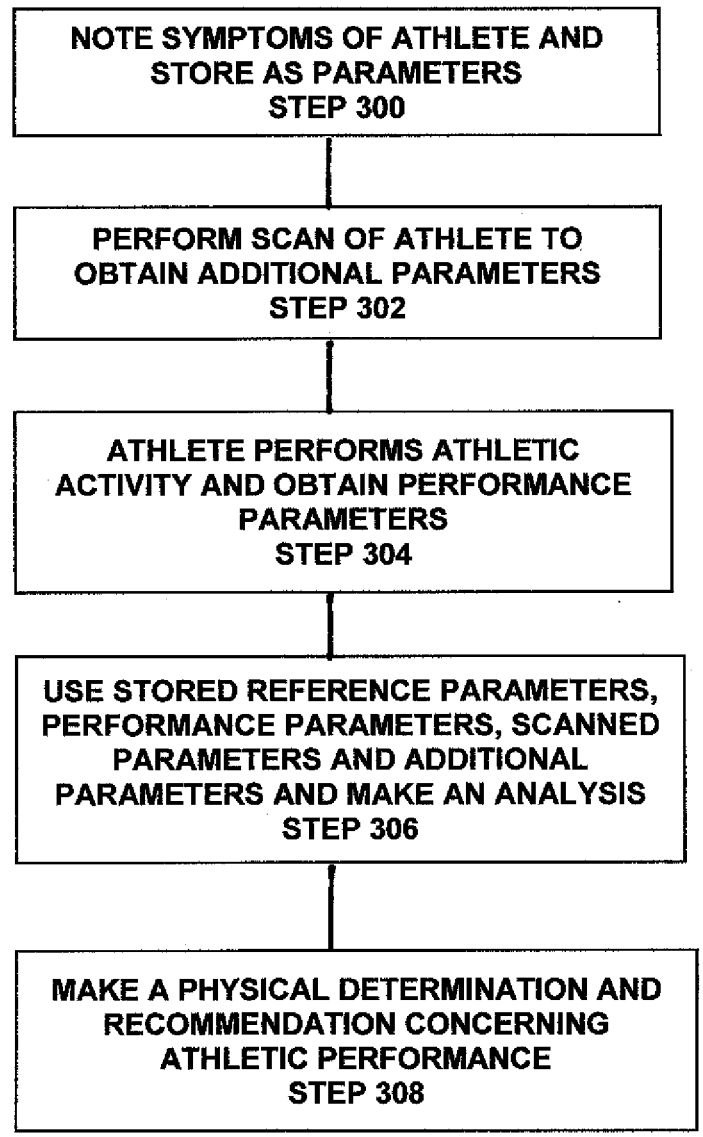
FIG. 7 is a flowchart showing the steps of obtaining parameters of an athletic, performance parameters of the athlete and using the obtained parameters with reference data to make a recommendation concerning the athletic performance of the athlete.

It has been found that pitching performance depends on both whole body "global" factors such as focus and stamina as well as "local" factors such as the biomechanics and physiology, such as for a baseball pitcher the pitching or throwing arm. In a preferred embodiment the method of the subject invention, as shown in FIG. 7, comprises the step of prior to performing an athletic activity, the athlete and/or the trainer notes any areas of symptoms (step 300), after which the scanning component performs surface and/or deep scans (step 302). It should be apparent to one skilled in the art that subjective or objective notations of symptoms, signs, or problems made by the athlete, physician, therapist, or trainer are optional and not crucial or necessary to the overall concept or spirit of the present invention. The athlete then performs an athletic activity, such as throwing a pitch or pitches, during which time a coach or trainer assesses the athlete's performance either via the current methods of naked eye assessment and/or via the use of a performance device of the performance scanning system (step 304), for example the performance device is a radar gun (to note the speed of a baseball) and/or a video recording device to note the accuracy and/or trajectory of the pitch. All these collected data are stored in the data storage system as reference data and the data analysis software module operates to perform an analysis which is displayed on an output device (step 306). In one preferred embodiment the data analysis software module functions to correlate certain parameters, such as arm temperature and/or arm temperature changes with performance parameters, such as baseball speed. For an illustrative example: k(arm temperature difference, current temp.−pre-pitching baseline temp.) equals baseball speed. It should be apparent to one skilled in the art that many such formulae may be used, for example: k(upper arm swelling difference, current upper arm swelling−baseline diameter of upper arm) equals speed. It should also be apparent to one skilled in the art that one or multiple formulae may be applied once, sequentially, or simultaneously, in any order, to derive useful comparisons and/or to draw many other conclusions (physical determinations) and using such physical determinations to make a recommendation, such as predicting future athletic performance and stopping a physical activity at a certain time (step 308).

In another non-limiting illustrative example, the athlete is a bodybuilder who wants to enlarge his/her muscles, either for training purposes or before a contest. The relevant surface (muscle area) is scanned using one or more scanning devices for obtaining collected data (parameters), such as swelling, then the athlete lifts weights to engorged the muscles with blood and to stimulate muscle growth. After lifting, the relevant surface (muscle area) is scanned again. The exact amount of parameter change (muscle size change (swelling)) and the location of these changes are detected and quantified by the data analysis software system, compared to the athlete's athletic performance level (such as the athlete's personal best size), such as an all-time biggest known size for the relevant muscle(s). The data analysis software module then operates to provide a recommendation such as if the athlete's current lifting program is providing the desired results.

In another non-limiting example, the performance scanning system is used to determine the appropriate amount of warm up in a relevant body part. For a non-limiting example, the athlete is a pitcher in a bullpen. The athlete is scanned repeatedly using the performance scanning system while warming up to decide when the athlete's throwing arm is at the best temperature or swelling for optimal performance (athletic performance level). In this example, the scanning device functions to scan the pitcher and the data analysis software module operates to analyze and compares the collected data (scanned parameters) to the athletic reference data, already found by earlier trials and stored in the data storage device, which exist in that particular athlete (pitcher) or athletes (pitchers) in general prior to the athlete's best performance.

In another non-limiting illustrated example, the performance scanning system is used similarly, as in the last example, to make a recommendation and interventions regarding rehabilitation therapies by comparing collected data and reference data to determine if the collected data (parameters) are approximating that athlete's pre-injury reference data (reference parameters) or approximating a population norm for appropriate rehab (reference data).

It should now be apparent that the performance scanning system of the subject invention operates to detect and quantify similarities or differences between collected data (parameters) obtained from an athlete (or a portion of an athlete) of interest and stored reference data and which can operate in a relative short amount of time and preferably in relative real time. In a preferred embodiment of the invention the performance system comprises one or more scanning devices for scanning and measuring various surface features of a portion of an athlete, including one or more of the following parameters: color, temperature, texture, size, shape, spatial dimensions, contour, curvature, softness, roughness, shininess/gloss, infrared signature, electrical vectors/flux, magnetic field strength/vector/flux, dynamic rebound, flexibility, spatial phase characteristics, measurements derived from spatial phase characteristics, and other such features. The performance scanning system comprises a data analysis software module using software and/or firmware capable of comparing parameters (data) retrieved from the athlete scanned to reference parameters or other representation comprising parameters from other similar or dissimilar athletes or from a previous scan(s) of the athlete. In a preferred embodiment of the invention the data analysis software module operates to determine the portion of the scanned athlete by comparing the parameters (data) from scanned athlete to various stored reference parameters. In another preferred embodiment, the performance scanning system of the subject invention further operates to determine differences between scanned parameters (data) obtained from two or more scans of the athlete.

In another preferred embodiment of the invention the data analysis software module operates to compare collected data retrieved from a scanned athlete to reference data that can include a representation comprising parameters from other similar or dissimilar athletes (reference data) and is capable of detecting and quantifying the similarities or differences between the collected data from the scanned athlete and stored reference data. It should now be apparent to one skilled in the art that such a performance scanning system can operate to permit the identification of a scanned portion of an athlete by comparing the scanned parameters (collected data) from the scanned athlete to various reference data. Preferably, the data analysis software module performs the method of representing the local topography of the surface of an athlete as a 2D histogram that is invariant to rigid transformations and creates model spin-images for the generation of plausible scanned-model point correspondence for use to generate pose estimates. Thus, it should now be apparent that two or more scans, such as scans showing parameters such as dimensions, color, temperature, and the like, can be placed in overlapping position using pose estimation allowing an image that shows changes to such parameters.

As shown and described above, the subject invention is a performance scanning system that operates to detect and measure parameters, such as surface parameters or deep scanning parameters, and uses the measured scanned parameters to determine the likelihood that the athlete's physical performance level has been or will be impaired. In a preferred embodiment of the invention the performance scanning system includes one or more performance devices that operate to measure and quantify athlete's performance level. Preferably, measured scanned parameters are correlated with performance parameters to make a physical determination of the likelihood that an athlete's physical performance level has or will deteriorate after an amount of time and/or determine if an athlete is physically at a condition to maximize the athlete's performance level, and/or if an athlete is physically at a condition that increases the possibility of injury.

As further shown, one or more scans of one or more portions of an athlete's anatomy (features) are taken to obtained scanned parameters and the scanned parameters are compared to other scans (reference data) and/or reference performance data relating to the athlete to make a physical determination of the likelihood that the athlete's performance level has been impaired or will soon be impaired. In another preferred embodiment of the invention correlating the performance of an athlete with one or more scanned parameters of a feature of the athlete's anatomy can be used to form a performance characteristic analysis record which can be used to make a physical determination that once certain scanned parameters reach a certain threshold, the athlete's performance level with deteriorate within a calculated amount of time or athletic activity. The performance characteristic analysis record then further operates in conjunction with scanned parameters to make a physical determination of the likelihood of injury to the athlete if athletic activity continues over a calculated period of time. The performance characteristic analysis record can then be used to make a physical determination if an athlete is physically at a condition to maximize the athlete's performance level.

It should now also be apparent that the performance scanning system of the subject invention provides a structured methodology and design utilized by the data analysis software module and is not limited solely to the specific design of the software. Although the foregoing invention has been described in some detail for purposes of clarity of understandings, it will be apparent that certain changes and modifications may be practiced within the scope of the appended claims. It should now be apparent that the various embodiments presented can be easily modified while keeping within the scope and spirit of the subject invention. Accordingly, it should be understood that the present disclosure is to be considered as exemplary of the principals of the invention and is not intended to limit the invention to the embodiments and the specific examples illustrated and the invention is not to be limited to the details given herein, but may be modified within the scope and equivalents of the descriptions and examples contained herein.

The invention claimed is:

1. A performance scanning system for use in analyzing and predicting the physical performance of an athlete, the performance scanning system comprising:
a computer system having a processor and memory;
a data storage device in communication with said computer system, wherein said data storage device includes reference data;
one or more scanning devices in communication with said computer system and operates to scan the athlete and obtain collected data of one or more features, wherein said collected data include measurements of scanned parameters of said one or more features of the athlete;
wherein said reference data includes performance parameters and measurements of previously scanned parameters for said one or more features of the athlete;
wherein said performance parameters and measurements of said previously scanned surface parameters are correlated to calculate athletic performance levels;
wherein the computer system then operates to compare said measurements of said scanned parameters with said measurements of said previously scanned parameters and uses said calculated athletic performance levels to make a determination predicting a performance level of the athlete.

2. The performance scanning system of claim 1, wherein said computer system further operates to compare said measurements of said scanned parameters with said measurements of said previously scanned parameters and makes a determination that said performance level of the athlete will drop within a certain amount time or an amount of continued athletic activity.

3. The performance scanning system of claim 1, wherein said determination is based on said scanned parameters that are weighted based on the significance of said scanned parameters to a physical activity.

4. The performance scanning system of claim 1, wherein said computer system operates to make a physical determination that indicates if the athlete is physically at a condition to maximize an athlete's athletic performance level.

5. The performance scanning system of claim 1, wherein said computer system operates to make a physical determination that indicates if the athlete is physically at a condition that increases the possibility of injury to the athlete.

6. The performance scanning system of claim 1, wherein said computer system operates to make a recommendation as to a type of an intervention that should be performed and transmits the recommendation to an output device.

7. The performance scanning system of claim 1, wherein said scanned parameters were taken at different time periods while the athlete is engaging in a physical activity.

8. The performance scanning system of claim 1, further comprising one or more performance devices that operate to obtain said performance parameters of an athlete and stores said performance parameters in said data storage device.

9. The performance scanning system of claim 1, further comprising a deep scanning system that operates to obtain deep scanning parameters, wherein said computer system operates to correlate said deep scanning parameters with said scanned parameters and said performance parameters and makes a physical determination that indicates the likelihood that the athlete's said performance level has been impaired or likely to be impaired within a predetermined amount of time.

10. The performance scanning system of claim 1, wherein said scanned parameters are weighted in accordance with their impact on athletic performance level or an athlete's likelihood of sustaining injury.

11. The performance scanning system of claim 1, wherein said computer system operates to make a determination as to differences between said previously scanned parameters and said scanned parameters of said collected data and displays such changes in an image.

12. A performance scanning system for use in analyzing and predicting the physical performance level of an athlete, the performance scanning system comprising:
- a computer system in communication with an analysis software module;
- a data storage device having reference data, wherein said reference data includes physical performance levels of the athlete;
- a scanning component having one or more scanning devices in communication with said computer system and operates to obtain measurements of scanned parameters of a feature of the athlete;
- one or more performance devices that operates to measure performance parameters of the athlete;
- wherein said analysis software module operates to use said measurements of said scanned parameters and said performance parameters to calculate a performance level of the athlete and to make a determination if said performance level has been impaired or will continue or will deteriorate after an amount of time or an amount of activity.

13. The performance scanning system of claim 12, wherein said scanning component includes a deep scanning system that operates to obtain deep scanning parameters; and
wherein said analysis software module operates to use said deep scanning parameters and said scanned parameters to make a physical determination of the athlete.

14. The performance scanning system of claim 13, wherein said physical determination indicates the likelihood that said performance level is impaired.

15. The performance scanning system of claim 13, wherein said physical determination indicates the likelihood that said performance level will deteriorate after a calculated amount of time.

16. The performance scanning system of claim 12, wherein said analysis software module operates to use said determination of the athlete to make a recommendation.

17. The performance scanning system of claim 12, wherein said determination indicates if the athlete is physically at a condition to maximize said performance level.

18. The performance scanning system of claim 12, wherein said determination indicates if the athlete is physically at a condition that increases the possibility of injury to the athlete.

19. The performance scanning system of claim 12, wherein said reference data includes baseline measurements of parameters of features of a portion of the athlete prior to the athlete engaging in an athletic activity.

20. A performance scanning system for use in analyzing and predicting the physical performance of an athlete, the performance scanning system comprising:
- a computer system in communication with an analysis software module;
- a data storage device having reference data, wherein said reference data includes physical performance levels of the athlete, wherein said physical performance levels are based on measurements of previous scanned parameters of a feature correlated with performance parameters;
- a scanning component having one or more scanning devices in communication with said computer system and operates to obtain collected data, wherein said collected data includes measurements of scanned parameters of the feature and deep scanning parameters of the feature;
- wherein said analysis software module operates to use said collected data and said reference data to determine a performance level of the athlete and to create a physical determination;
- wherein said physical determination indicates one or more of the following: the likelihood that the athlete's said performance level is impaired, the likelihood that the athlete's said performance level will deteriorate after a calculated amount of time, if the athlete is physically at a maximum performance level, and if the athlete is physically at a condition that increases the possibility of injury to the athlete.

* * * * *